(12) United States Patent
Von Drasek

(10) Patent No.: US 10,590,007 B2
(45) Date of Patent: Mar. 17, 2020

(54) CONTROL OF INDUSTRIAL WATER TREATMENT VIA DIGITAL IMAGING

(71) Applicant: Ecolab USA Inc., St. Paul, MN (US)

(72) Inventor: William A. Von Drasek, Oak Forest, IL (US)

(73) Assignee: Ecolab USA Inc., Saint Paul, MN (US)

( * ) Notice: Subject to any disclaimer, the term of this patent is extended or adjusted under 35 U.S.C. 154(b) by 0 days.

(21) Appl. No.: 15/654,063

(22) Filed: Jul. 19, 2017

(65) Prior Publication Data

US 2018/0022621 A1 Jan. 25, 2018

Related U.S. Application Data

(60) Provisional application No. 62/364,138, filed on Jul. 19, 2016.

(51) Int. Cl.
*C02F 1/00* (2006.01)
*G01N 25/18* (2006.01)
(Continued)

(52) U.S. Cl.
CPC ............... *C02F 1/008* (2013.01); *C02F 1/50* (2013.01); *C02F 5/08* (2013.01); *G01N 21/85* (2013.01);
(Continued)

(58) Field of Classification Search
CPC .... C02F 1/008; C02F 1/50; C02F 5/08; C02F 2209/02; C02F 2101/203; G01N 21/85;
(Continued)

(56) References Cited

U.S. PATENT DOCUMENTS

| 4,836,146 A | * | 6/1989 | Russell | ................... F22B 37/56 122/379 |
| 5,174,654 A | | 12/1992 | Droege | |

(Continued)

FOREIGN PATENT DOCUMENTS

| JP | 3181543 B2 | 7/2001 |
| WO | 2005085804 A1 | 9/2005 |
| WO | WO 2011/018592 A1 | 2/2011 |

OTHER PUBLICATIONS

Choi et al., "Morphological analysis and classification of types of surface corrosion damage by digital image processing," *Corrosion Science*, 47, pp. 1-15 (2005.
(Continued)

*Primary Examiner* — Qian Yang
(74) *Attorney, Agent, or Firm* — Fredrikson & Byron, P.A.

(57) ABSTRACT

Systems for and methods of monitoring and analyzing deposit in an industrial water system are provided. The methods comprise heating a substrate while the substrate contacts industrial water in the industrial water system to form deposit on the substrate. A series of digital images of the substrate while the substrate contacts the industrial water in the industrial water system is created. A region of interest in the series of digital images of the substrate is defined. A deposit feature in the region of interest in the series of digital images of the substrate is identified. The deposit feature in the region of interest in the series of digital images of the substrate is analyzed to determine a deposit trend of the substrate in the industrial water system. Generally, the systems are configured so as to be capable of carrying out one or more of the methods.

20 Claims, 6 Drawing Sheets

(51) Int. Cl.

| | |
|---|---|
| *G01N 21/85* | (2006.01) |
| *C02F 1/50* | (2006.01) |
| *C02F 5/08* | (2006.01) |
| *G06K 9/20* | (2006.01) |
| *G06K 9/46* | (2006.01) |
| *G06K 9/62* | (2006.01) |
| *G01N 33/18* | (2006.01) |
| *C02F 101/20* | (2006.01) |

(52) U.S. Cl.
CPC ............ *G01N 25/18* (2013.01); *G06K 9/209* (2013.01); *G06K 9/2054* (2013.01); *G06K 9/46* (2013.01); *G06K 9/6267* (2013.01); *C02F 2101/203* (2013.01); *C02F 2209/02* (2013.01); *G01N 33/18* (2013.01)

(58) Field of Classification Search
CPC ........ G01N 33/18; G06K 9/46; G06K 9/6267; G06K 9/2054; G06K 9/209
See application file for complete search history.

(56) References Cited

U.S. PATENT DOCUMENTS

| | | | |
|---|---|---|---|
| 5,248,198 A | 9/1993 | Droege | |
| 5,278,074 A | 1/1994 | Rao et al. | |
| 5,320,779 A | 6/1994 | Fivizzani | |
| 5,332,900 A | 7/1994 | Witzke et al. | |
| 5,360,549 A | 11/1994 | Mouche et al. | |
| 5,399,017 A | 3/1995 | Droege | |
| 5,734,098 A | 3/1998 | Kraus et al. | |
| 5,750,070 A | 5/1998 | Tang et al. | |
| 5,992,505 A | 11/1999 | Moon | |
| 6,034,775 A | 3/2000 | McFarland et al. | |
| 6,068,012 A * | 5/2000 | Beardwood ............ | G05D 21/02 137/3 |
| 6,143,800 A | 11/2000 | Nguyen et al. | |
| 6,250,140 B1 | 6/2001 | Kouznetsov et al. | |
| 6,336,058 B1 | 1/2002 | Fowee | |
| 6,375,829 B1 | 4/2002 | Shevchenko et al. | |
| 6,448,411 B1 | 9/2002 | Meyer | |
| 6,488,868 B1 | 12/2002 | Meyer | |
| 6,599,445 B2 | 7/2003 | Meyer | |
| 6,696,572 B2 | 2/2004 | Meyer | |
| 6,740,231 B1 | 5/2004 | Bauman et al. | |
| 6,792,357 B2 | 9/2004 | Menon et al. | |
| 6,942,782 B2 | 9/2005 | Shevchenko et al. | |
| 7,077,563 B2 | 7/2006 | Xiao et al. | |
| 7,135,683 B2 | 11/2006 | Davis et al. | |
| 7,563,377 B1 * | 7/2009 | Simpson ................. | C02F 1/683 134/3 |
| 7,842,127 B2 | 11/2010 | Malwitz | |
| 7,842,165 B2 | 11/2010 | Shevchenko et al. | |
| 8,585,930 B2 | 11/2013 | Tiwari | |
| 8,618,027 B2 | 12/2013 | Meyer et al. | |
| 8,945,371 B2 * | 2/2015 | Kouznetsov ............ | H01L 41/04 162/198 |
| 8,958,898 B2 | 2/2015 | Von Drasek et al. | |
| 9,074,289 B2 | 7/2015 | Malwitz et al. | |
| 9,175,405 B2 | 11/2015 | Gill et al. | |
| 2005/0245411 A1 | 11/2005 | Yang et al. | |
| 2006/0241874 A1 | 10/2006 | Carter | |
| 2006/0281191 A1 | 12/2006 | Duggirala et al. | |
| 2008/0308770 A1 | 12/2008 | Tiwari | |
| 2009/0158827 A1 | 6/2009 | Dermody et al. | |
| 2011/0274138 A1 | 11/2011 | Auret et al. | |
| 2011/0286492 A1 | 11/2011 | Auret et al. | |
| 2012/0073775 A1 | 3/2012 | Duggirala et al. | |
| 2012/0258547 A1 | 10/2012 | Von Drasek et al. | |
| 2014/0037037 A1 * | 2/2014 | Ito ......................... | G21C 19/32 376/306 |
| 2014/0177673 A1 | 6/2014 | Bliss et al. | |
| 2014/0272133 A1 | 9/2014 | Gill et al. | |
| 2014/0293040 A1 * | 10/2014 | Hietaniemi ............ | G01N 15/04 348/88 |
| 2014/0326667 A1 * | 11/2014 | Richmond ................ | C02F 9/00 210/638 |
| 2014/0368823 A1 * | 12/2014 | Wirthlin ................. | G01N 21/55 356/448 |
| 2016/0347716 A1 | 12/2016 | Harbindu et al. | |
| 2016/0348251 A1 | 12/2016 | Seetharaman et al. | |
| 2016/0348252 A1 | 12/2016 | Rane et al. | |
| 2016/0348253 A1 | 12/2016 | Harbindu et al. | |

OTHER PUBLICATIONS

Fontana, "Table 4-5—Comparison of mils penetration per year (mpy) with equivalent metric-rate expressions," *Corrosion Engineering*, Third Edition, McGraw-Hill Book Company, New York, p. 172 (1986).

Garcia-Antón et al., "Online Visualization of Corrosion Processes of Zinc and a Cu/Zn Galvanic Pair in Lithium Bromide Solutions," *Corrosion*, 59(2), pp. 172-180 (Feb. 2003).

Isaacs et al., "Direct Image Processing of Corroding Surfaces Applied to Friction Stir Welding," BNL-72208-2004-CP, http://www.bnl.gov/isd/documents/26303.pdf, 7 pp. (2004).

Nalco, "ASTM G1-03—Standard Practice for Preparing, Cleaning, and Evaluating Corrosion Test Specimens," ASTM International, West Conshohocken, Pennsylvania, pp. 17-25 (2003).

Sullivan et al., "In situ monitoring of the microstructural corrosion mechanisms of zinc-magnesium-aluminum alloys using time lapse microscopy," *Corrosion Science*, 53, pp. 2208-2215 (2011).

Cicek et al., "Characterization Studies of Mild Steel Allow Substrate Surfaces Treated by Oxyanion Esters of [alpha]-Hydroxy Acids and Their Salts," Int'l J. of Chemical Science and Tech., 2(3), pp. 244-260. (Oct. 1, 2012).

Ott et al., "Modifications to the Copper Strip Corrosion Test for the Measurement of Sulfur-Related Corrosion," J. of Sulfur Chem., 28(5), pp. 493-504 (Oct. 1, 2007).

Rivas et al., "Extreme value analysis applied to pitting corrosion experiments in low carbon steel: Comparison of block maxima and peak over threshold approaches," Corrosion Science, 50, pp. 3193-3204 (2008).

Van Der Merwe et al., "Comparison of Linear Polarization Resistance Corrosion Monitoring Probe Readings and Immersion Test Results for Typical Cooling Water Condition," J. of the Southern African Inst. of Mining and Metallurgy, 115, pp. 173-178 (Mar. 1, 2015).

International Patent Application No. PCT/US2017/042793, International Search Report and Written Opinion dated Oct. 20, 2017, 13 pages.

* cited by examiner

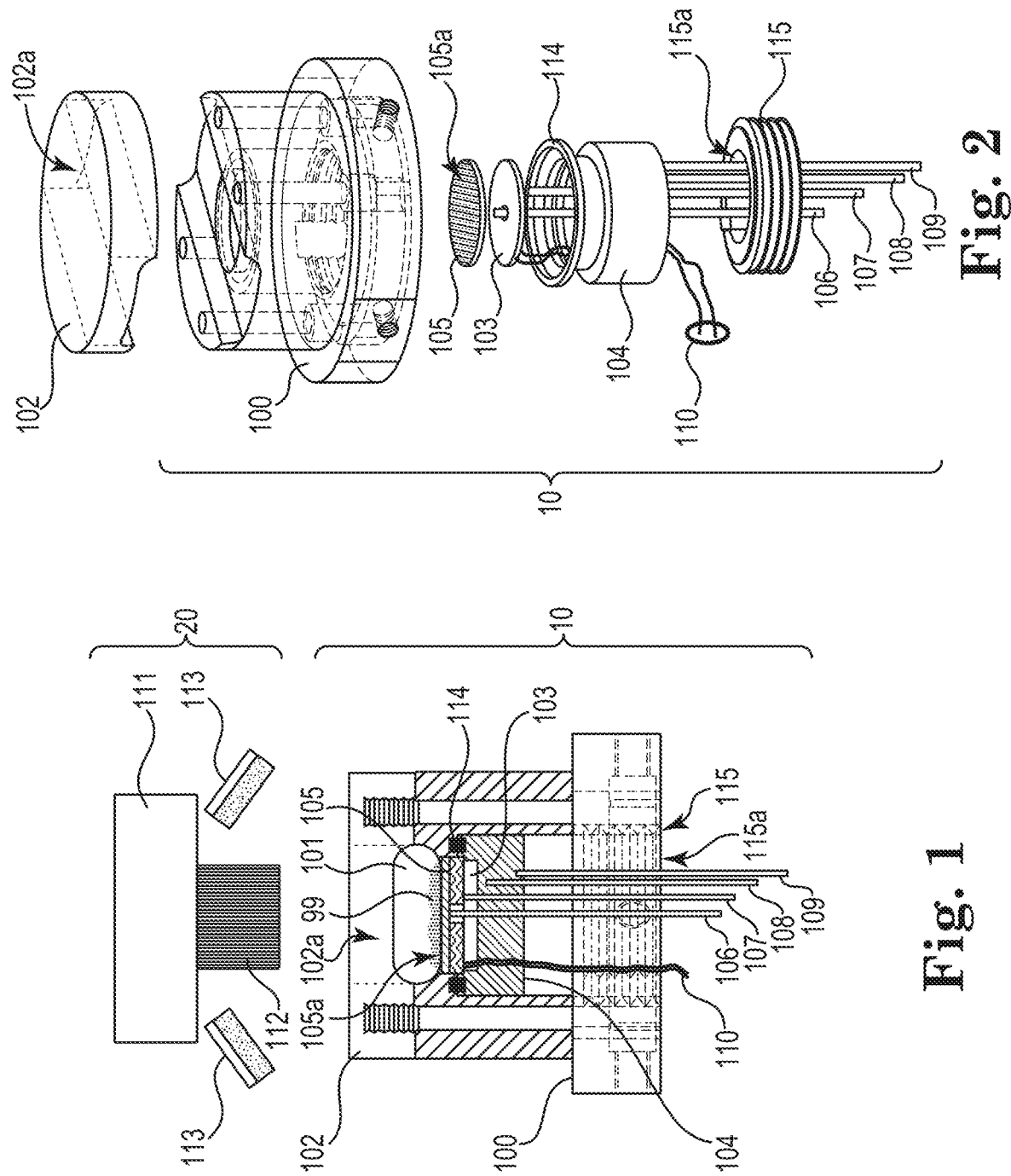

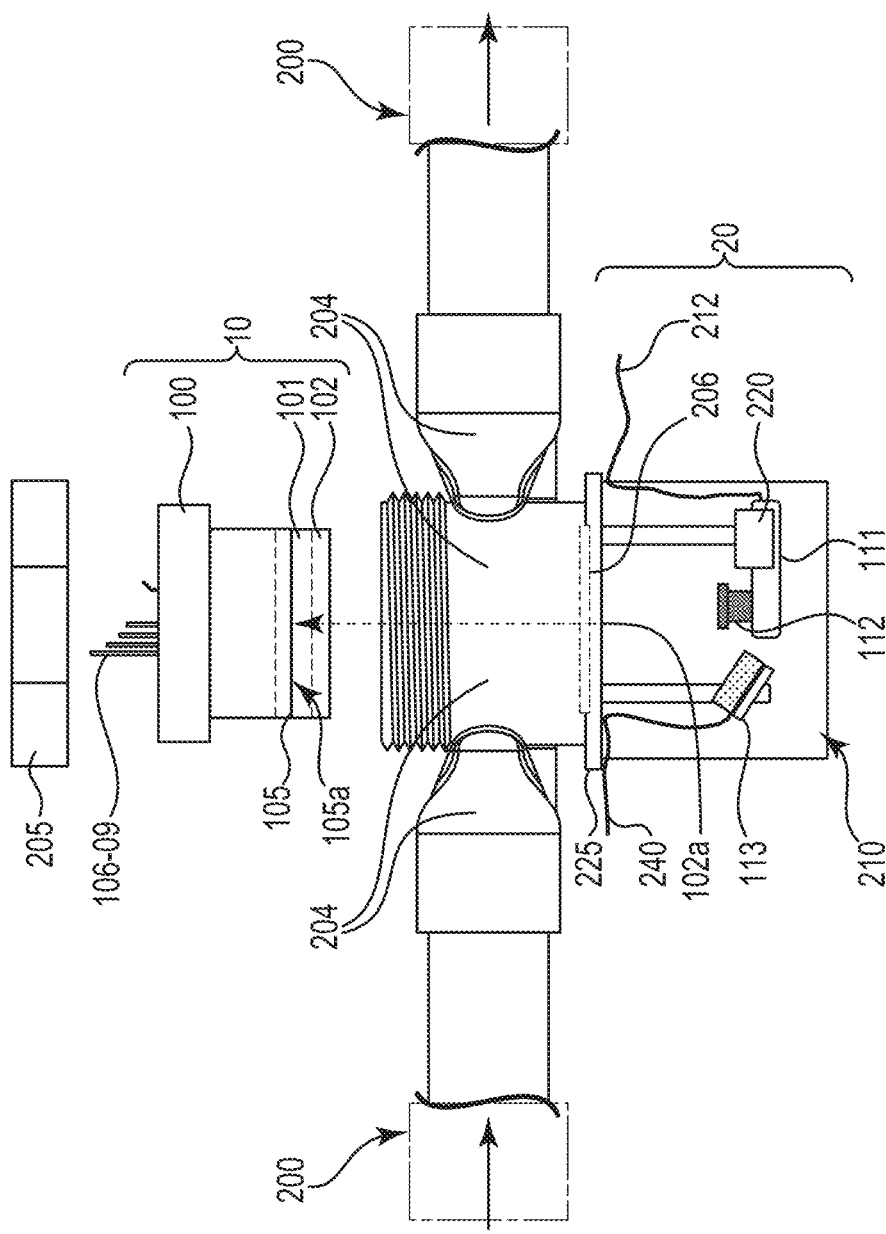

CONTROL OF INDUSTRIAL WATER TREATMENT VIA DIGITAL IMAGING

This application is a nonprovisional application claiming the benefit of U.S. Provisional Patent Application Ser. No. 62/364,138, filed Jul. 19, 2016, the disclosure of which is incorporated herein by reference in its entirety.

BACKGROUND

Maintaining deposit-free heat exchange surfaces in water systems, particularly in industrial water systems, e.g., cooling water systems and heating water systems, is important to optimizing energy efficiency. Mineral deposit, particularly calcium salts, and more particularly calcium carbonate, may be in the form of scaling or fouling. Generally, scaling is the precipitation of inorganic salts on equipment surfaces, and fouling results from deposit of insoluble particles suspended in a liquid. Monitoring industrial water systems to minimize or prevent deposit (mineral or otherwise) onto heat exchange surfaces can provide information that can be utilized to improve, or at least maintain, efficiency in an industrial water system's operation and/or treatment program.

Biofilm deposit onto heat exchange surfaces can also cause inefficiency in industrial water systems. For example, compared to mineral deposit, biofilm deposit is generally a 4 to 5 times better insulator than mineral deposit. Generally, biofilms are slimy, and the microorganisms causing the formation of a biofilm may represent merely a small fraction of the biofilm's content.

SUMMARY

The invention is directed to using digital imaging of a substrate to analyze deposit in an industrial water system. In certain embodiments, the invention uses digital imaging of a substrate to determine heat transfer resistance of the substrate, which can be utilized to correlate to heat transfer resistance that may result from deposit.

A method of analyzing deposit on a substrate contacting industrial water in an industrial water system is provided. The method comprises creating a digital image of the substrate while the substrate contacts the industrial water in the industrial water system. A region of interest in the digital image of the substrate is defined. A deposit feature in the region of interest in the digital image of the substrate is identified. The deposit feature in the region of interest in the digital image of the substrate is analyzed.

A method of analyzing deposit on a substrate contacting industrial water in an industrial water system is provided. In certain embodiments, the method comprises heating the substrate while the substrate contacts the industrial water in the industrial water system to form deposit on the substrate. A series of digital images of the substrate while the substrate contacts the industrial water in the industrial water system is created. A region of interest in the series of digital images of the substrate is defined. A deposit feature in the region of interest in the series of digital images of the substrate is identified. The deposit feature in the region of interest in the series of digital images of the substrate is analyzed to determine a deposit trend of the substrate in the industrial water system.

A system for monitoring deposit in an industrial water system is provided. The system comprises a fluid flow channel having optical access. A heated substrate is configured to contact industrial water present in the fluid flow channel. A camera is configured to capture digital images of the substrate when located in the fluid flow channel. A plurality of temperature sensors is configured to measure a temperature gradient across the heated substrate.

BRIEF DESCRIPTION OF THE SEVERAL VIEWS OF THE DRAWINGS

FIG. 1 is a schematic view of an embodiment of a system that may be utilized to carry out a method described herein.

FIG. 2 is an exploded view of a portion of a system that may be utilized to carry out the methods described herein.

FIG. 3. is a partially-exploded schematic of a system that may be utilized to carry out the methods described herein.

DETAILED DESCRIPTION

Figure 4:
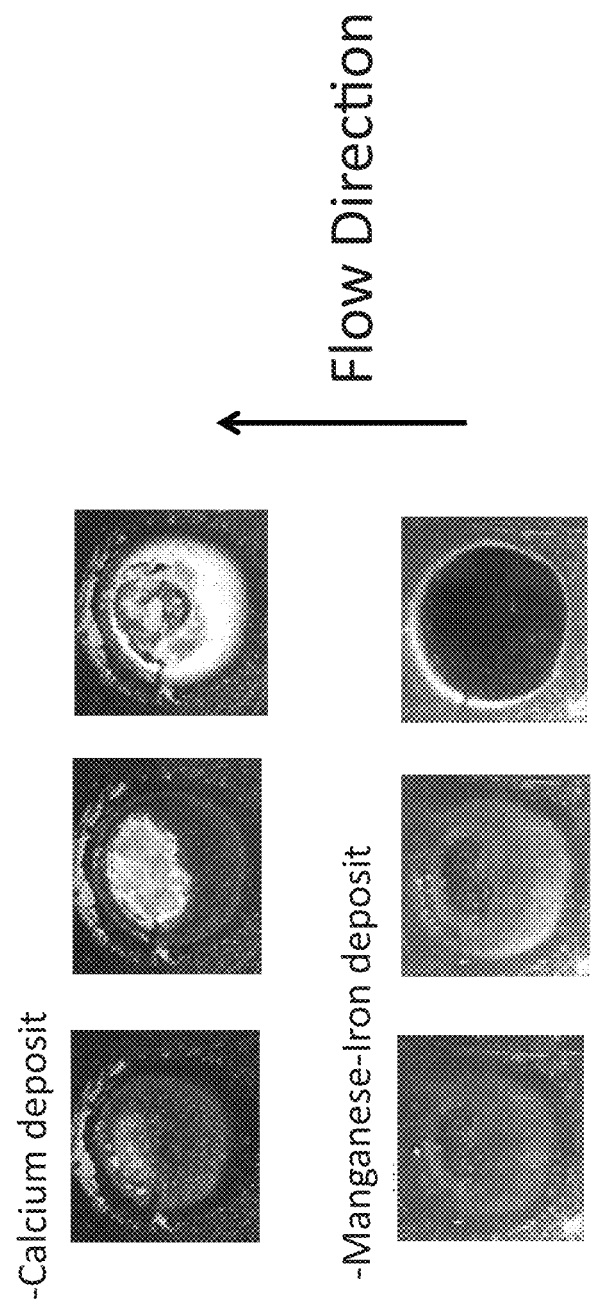
FIG. 4 shows examples of images differentiating calcium deposit from manganese-iron deposit.

The invention is directed to using digital imaging of a substrate to analyze deposit in an industrial water system. In certain embodiments, the invention uses digital imaging of a substrate to determine heat transfer resistance of the substrate, which can be utilized to correlate to heat transfer resistance that may result from deposit.

A method of analyzing deposit on a substrate contacting industrial water in an industrial water system is provided. The method comprises creating a digital image of the substrate while the substrate contacts the industrial water in the industrial water system. A region of interest in the digital image of the substrate is defined. A deposit feature in the region of interest in the digital image of the substrate is identified. The deposit feature in the region of interest in the digital image of the substrate is analyzed.

A method of analyzing deposit on a substrate contacting industrial water in an industrial water system is provided. In certain embodiments, the method comprises heating the substrate while the substrate contacts the industrial water in the industrial water system to form deposit on the substrate. A series of digital images of the substrate while the substrate contacts the industrial water in the industrial water system is created. A region of interest in the series of digital images of the substrate is defined. A deposit feature in the region of interest in the series of digital images of the substrate is identified. The deposit feature in the region of interest in the series of digital images of the substrate is analyzed to determine a deposit trend of the substrate in the industrial water system.

Provided are systems for and methods of analyzing deposit on a substrate contacting industrial water in an industrial water system. In certain embodiments, the method is a method of quantifying deposit on a substrate contacting industrial water in an industrial water system. The phrases "analyzing," "defining," "synthesizing," and "quantifying," and related terminology (e.g., conjugate forms), are used herein to describe aspects of the methods, with "analyzing"

being inclusive of "quantifying," "defining," and "synthesizing," which are all subsets of analyzing. The term "substrate," "coupon," and similar terms are to be construed as including "or a portion thereof."

A system for monitoring deposit in an industrial water system is provided. The system comprises a fluid flow channel having optical access. A heated substrate is configured to contact industrial water present in the fluid flow channel. A camera is configured to capture digital images of the substrate when located in the fluid flow channel. A plurality of temperature sensors is configured to measure a temperature gradient across the heated substrate.

An illustrative embodiment of a system for monitoring deposit in an industrial water system is shown in FIGS. 1 and 2. The system comprises, among other things, probe body 100 with flow channel 101 for fluid to enter and exit. Heating element 103 is mounted on a support medium with low thermal conductivity. Heating element 103 can be a cartridge, ceramic, mica, or any of variety of heating devices. Substrate 105 is in direct contact with heating element 103 on one side, with liquid (e.g., industrial water) flowing through flow channel 101 and contacting a surface of substrate 105. Substrate 105 may be a separate piece or, e.g., a "built-in" portion of the equipment that forms flow channel 101. In certain embodiments of the system, the substrate is constructed of a suitable metal, alloy, or ceramic material. The substrate may be constructed to have a user specified surface finish and/or roughness.

Heating element 103 and substrate 105 can be mounted using, e.g., a low thermal conducting support 104. Preferably, support 104 inserts into probe body 100 such that a surface of substrate 105 (i.e., surface 105a) is flush with flow channel 101. In the illustrated embodiment, ring 114 may be outfitted with an o-ring to form a seal between support 104 and probe body 100 to constrain fluid in flow channel 101.

In certain embodiments of the systems described herein, a portion of the system is constructed so as to be removable from the rest of the system. For example, the camera and/or light source(s) and/or plurality of temperature sensors may be removable as one or more units from the rest of the system.

In the illustrated embodiment, temperature probes 106, 107, 108, and 109 are mounted on the support block to measure temperature at different locations. Though the illustrated embodiment includes four temperature probes, less (e.g., 2 or 3) or more (e.g., 5, 6, 7, . . . , n) can be utilized. As shown, temperature probe 106 makes direct contact with substrate 105 through a hole in heating element 103. Temperature probe 107 makes direct contact with the backside of heating element 103 and temperature probes 108 and 109 are mounted at different locations in the support 104 to measure the heat flux through support 104. Connection leads 110 of heating element 103 exit through support 104 for connecting to a power supply.

With continued reference to FIGS. 1 and 2, flow channel 101 is made by mounting a plate 102 to probe body 100. Plate 102 can be fabricated out of, e.g., clear acrylic material or a modified mounting piece with a clear window such as glass, quartz, sapphire, acrylic, such that plate 102 provides optical access 102a to view surface 105a of substrate 105. Heating element 103 and substrate 105 can be assembled, e.g., using high thermal conducting epoxy, e.g., DURALCO 128 or 132 epoxy, supplied by Cotronics Corp., 131 47th street, Brooklyn, N.Y. The heater-substrate assembly can then be epoxied into support 104 using DURALCO 4525 or 4538 epoxy. The heater-substrate-support assembly (i.e., assembly 10) can then be mounted into probe body 100, e.g., via retaining nut 115. As illustrated, retaining nut 115 is notched to allow the temperature probes 106, 107, 108, 109 and connection leads 110 of heating element 103 to pass through notch 115a. A liquid tight seal is made by tightening retaining nut 115 to compress o-ring 114 against probe body 100 and support 104.

In some cases, an automated in-situ cleaning process may be applied to plate 102. Generally, deposit from a substrate surface may be removed under acidic conditions. Acidic conditions can be generated by injecting acid into the industrial water contacting the substrate surface. However, the aforestated approach tends to add complexity, requiring automated valves, a delivery system (pump(s), etc.), and an acid supply onsite. A more convenient approach utilizes electrochemical cleaning by applying a potential between the metal substrate and a counter-electrode. For cleaning, the metal substrate is the anode and a counter-electrode cathode is integrated into the system. The counter-electrode can be constructed of, e.g., metal (e.g., stainless steel), graphite, or conductive glass (e.g., indium tin oxide or fluorine doped tin oxide). Using conductive glass provides dual functionality as a window for optical access to view the substrate surface as well as a counter-electrode for electrochemical cleaning. When utilized, the conductive glass can be, e.g., coated with anti-reflective substance.

FIG. 3 shows assembly 10 made up of the components outlined in FIGS. 1 and 2 that are configured to attach to conduit 200 of, e.g., an industrial water system, via interfaces 204. In the illustrated embodiment, interfaces 204 are keyed such that assembly 10 is oriented to allow fluid passing through flow channel 101. Interfaces 204 connect to standard piping and provide transitions from round to square geometry, and vice versa, while maintaining the same cross-sectional area. Assembly 10 can be attached to interfaces 204 via nuts 205. O-rings (not shown) can be utilized to provide seals between assembly 10 and interfaces 204.

On one side of interfaces 204, window 206 provides optical access 102a to plate 102 through to surface 105a of substrate 105, thus, providing the ability to view surface 105a of substrate 105 in flow channel 101 during operation.

As shown, imaging system 20 comprises camera 111 with lens 112 and optional illumination sources 113. Though two illumination sources 113 are shown, less (e.g., 0 or 1, with one illumination source 113 shown in FIG. 3) or more (e.g., 3, 4, . . . , n) may be utilized with imaging system 20. Positioning imaging system 20 in the illustrated manner allows for imaging surface 105a of substrate 105 during operation (e.g., while exposed to fluid flowing through flow channel 101).

Multiple illumination sources 113 may be used to illuminate from different direction to accentuate the desired features on the substrate or surface thereof, or to improve the overall illumination profile. For example, illuminating a surface of the substrate with an illumination source positioned near perpendicular to the surface can provide a bright field illumination. In this case, the imaging device captures most of the direct reflected light. Placing one or more illumination sources with large angle(s) of incidence relative to the surface normal can enhance salient features, such as scratches, pits, and/or deposit morphology, on the surface. In addition, the light can be directional or diffuse. Diffuse lighting provides more uniform illumination and attenuates the specular component when illuminating reflective surfaces. The light may be sourced from one or more of a light emitting diode ("LED"), an incandescent bulb, a tungsten halogen bulb, light transported via fiber optic or any combination of these or other standard means to provide illumination.

An example of an LED light source is available as CREEXPE2-750-1 from Cree, Inc., 4600 Silicon Drive Durham, N.C. 27703, which in certain embodiments is equipped with a Carclo lens model 10138, available from Carclo Optics, 6-7 Faraday Road, Rabans Lane Industrial Area, Aylesbury HP19 8RY, England, U.K.

Illumination sources 113 may be mounted so as to allow for angle and height adjustment. The light emission wavelength spectrum can cover the white light region or specific wavelength bands to highlight specific features. For example, specific wavelengths can be used to highlight color on the coupon surface or used with black and white camera to extract color information from the surface. In certain embodiments presented herein, the substrate is lit with light having a wavelength band of from about 390 nm to about 700 nm.

Image acquisition control can be made by a PC, microprocessor, external controller, and/or embedded processor in the camera. Commercial digital cameras generally come standard with image acquisition speeds 30 frames per second ("fps") or greater. Because deposit generally occurs at a much longer time scale (e.g., 10 s of minutes to weeks), image acquisition control is the preferred method, i.e., acquiring a single image or average of N images at a frequency that can be, e.g., fixed, variable, and/or event driven. Collecting data in this manner utilizes data storage more efficiently. For example, an image acquisition rate of once per day, or once per week, may be sufficient for certain industrial water systems if only gross changes in deposit features are of interest. However, if the industrial water system experiences an upset, e.g., a drop in pH, the dynamics of the deposit features can be missed with infrequent image acquisition. In this case, triggering an increase in the frequency of the creation of the digital images at the time of upset allows for collecting image data at a finer time resolution. Electrical power and/or communication can be provided to components of the imaging system by cabling connections and/or antennas.

Additional illumination control can be provided via the utilization of filters and/or polarizers on light source(s) (e.g., attached to lens 109) and/or via imaging device 106. For example, adding a linear polarizers can allow for the removal of reflections or hot spots (e.g., high light intensity glare) from the image originating from the light source rays that, e.g., may reflect off the transparent window or pipe. Additionally or instead, color filters (e.g., bandpass, notch, shortpass, and/or longpass) may be used to enhance specific image detail or remove background light effects. Filtering can be applied on the camera, light source, or both. For example, red features on a surface can be enhanced using a light source with a bandpass or longpass filter greater than 600 nm, e.g., 600-1100 nm, or more preferably 600-700 nm, and even more preferably, 630 nm. In this case, the red light will reflect off the red surfaces of the substrate to the imaging detection device that can also be equipped with a similar filter. This allows only the reflected light from the surface in the wavelength transmission range of the filter to reach the detector, resulting in red feature enhancement.

As shown in FIG. 3, imaging device 20 may further comprise mount 220. Mount 220 may be immovable or movable. As illustrated, mount 220 is movable so as to provide focusing capability of imaging device 20. As shown in FIG. 3, mount 220 and illumination source 113 are mounted to base 225. Imaging device 20 can be enclosed via cover 210. The powered components of imaging system can be connected to power and communication ports, e.g., via wiring 240. While an autofocusing camera may obviate the need for using a movable mount, an autofocus camera may be used with an immovable or movable mount.

Camera 111 can be CMOS, CCD, Silicon PDA, or any array style detector that provides spatial light intensity information. Commercial cameras that use either CMOS or CCD technology are readily available and provide image data when coupled with a lens (e.g., lens 112). Camera 111 can be integrated with a computer for image acquisition and processing or utilize embedded processing where a dedicated processer is present in camera 111. The creation of a series of digital images may be made, e.g., by a set scheduled time (e.g., once per hour) or triggered based on an event (e.g., when pH is detected outside a control range).

The digital image, or series thereof, provides evidence of the presence or absence of deposit on the substrate (e.g., deposit 99 on surface 105a of substrate 105). The digital image, or series thereof, can provide further insight into, e.g., type of deposit based on color and/or morphology, early onset of deposit formation, percent coverage on the surface, and estimated thickness based on depth of focus.

An aspect of the methods provided herein allows for accelerated formation of deposit on the substrate by heating the substrate. Accelerated formation of deposit can provide information to the user that can be utilized to take action to prevent the formation of deposit in critical heat transfer equipment, e.g., a heat exchanger, a condenser, a cooling tower, etc.

Applying power to heating element 103 creates a local temperature differential between substrate 105 and fluid located in flow channel 101, with the substrate area having a higher temperature than the fluid flowing through flow channel 101. In applications involving salts with inverse-solubility characteristics (e.g., calcium salts, more particularly, calcium carbonate, calcium sulfate, calcium phosphate, etc.), precipitation on surface 105a of substrate 105 can occur, which results in the formation of deposit 99. As deposit 99 forms on surface 105a of substrate 105, the temperature of substrate 105 will increase because of the reduced thermal conductivity, i.e., insulating properties of deposit 99, which reduces the convective heat removal from substrate 105. The temperature gradient can be measured using a plurality of temperature probes (e.g., temperature probes 106, 107, 108, 109). The plurality of temperature probes may be one or more of any suitable type of temperature probes, e.g., thermocouple, resistance temperature detector ("RTD"), fiber optic temperature probe, infrared temperature probe, or any suitable temperature measurement device. Measuring substrate 105 temperature and knowing the fluid temperature and flow conditions in or near flow channel 101, the heat transfer resistance ("HTR") due to deposit 99 can be determined using mathematical transformation(s).

For example, to determine the heat transfer resistance of deposit on the substrate a heat flow analysis is applied starting with $$Q_{electric} = Q_{out\,water} + Q_{loss} \qquad (1)$$

where $Q_{electric}$ is the heater power determined from the input voltage to the heater and the heater resistance, $Q_{out\,water}$ is the heat removed to the water flow stream above the substrate, and $Q_{loss}$ is the heat lost through the heater support structure. To simplify the analysis, a one-dimensional heat flow is assumed, i.e., flow in the radial direction and losses through the sides are assumed negligible ($Q_{loss}=0$), to illustrate the basic concept. Using Fourier's law $Q_{out\ water}$ in Equation (1) gives the total HTR as $$HTR_{Total} = \frac{1}{U} = \frac{A\Delta T}{Q_{electric}} \quad (2)$$

where $HTR_{total}$ is the reciprocal of the overall heat transfer coefficient and is the sum of all heat transfer resistances of certain materials, such as the substrate, heater, mount, convection, and deposit. A is the area of the heated surface and $\Delta T$ is the temperature difference between the heater and bulk fluid flowing across the substrate. For a clean substrate $HTR_{deposit}=0$ and $HTR_{total}$ is then given by $$HTR_{total}=HTR_{heater}+HTR_{substrate}+HTR_{mount}+HTR_{convection} \quad (3)$$

To determine the fixed HTR values (heater, substrate, and mount) the convective terms is calculated from the Nusselt number (Nu) having a general expression as $$Nu = \frac{hl}{k} = CRe^m Pr^n \quad (4)$$

where C, m, and n are constants determined experimentally, l is the length, k is the fluid thermal conductivity, h is the convective heat transfer, Re is the Reynolds number, and Pr is the Prandtl number. Nusselt number correlations can be found in the literature for different geometries and Reynold number ranges. Knowing the fluid physical properties and flow conditions, the $HTR_{convection}$ (1/h) is calculated from Equation (4). The fixed heat transfer resistance for a clean substrate is given by $$HTR_{fixed}=HTR_{total}-HTR_{convection} \quad (5)$$

The change in heat transfer resistance at time, t, is then $$HTR_t=HTR_{total}-HTR_{fixed}-HTR_{convection} \quad (6)$$

The heat transfer resistance of the deposit is then determined by measuring identical conditions for a clean substrate and a substrate having deposit:

$$HTR_{deposit}=HTR_{t,deposited}-HTR_{t,clean} \quad (7)$$

When coupled with in-situ cleaning (e.g., electrochemical, chemical, air, ultrasonic, mechanical, etc.) to remove deposit formed on the surface, the digital image, or series thereof, can provide feedback on the state of deposit removal, e.g., whether the deposit is completely removed or is still present, which can be used to trigger stoppage of the in-situ cleaning process. If the image data indicates deposit is still present on the substrate, the cleaning operation can continue until a desired level of cleanliness is reached.

The digital image, or series thereof, can also provide insight into the type of deposit based on color and/or morphology of the deposit. Using data related to the digital image, or series thereof, along with knowledge of water chemistry and treatment can allow for the identification of the deposit composition. For example, a white crystalline deposit is a good indicator that the deposit is likely from calcium salt whereas a dark brownish deposit could indicate high manganese and/or iron content. Generally, biofilm will have a different reflective characteristic due to the slimy nature of microbiological deposit. Combining this observed change in combination with, e.g., low oxidation-reduction potential measurement provides credence that the deposit is at least partially microbiological in origin, because microbiological deposits generally comprise multiple components, e.g., mineral, silt, and microbiological components.

Thus, in certain embodiments of the methods and systems, multiple methods and/or systems are utilized so as to allow for differentiation of type(s) of deposits. For example, a plurality of systems operating at different heated substrate temperatures may be implemented so as to analyze a plurality of deposit formations. At a relatively low temperature range (e.g., from about 30° C. to about 50° C.) tends to provide conditions for biofilm growth, whereas a relatively high temperature range (e.g., from about 70° C. to about 120° C.) tests the water potential for mineral scale.

The method of collecting and analyzing the substrate image data is not limited to the configuration shown in the figures, or to a heat transfer resistance measurement device. For example, deposit imaging can be conducted on a quartz crystal microbalance ("QCM," such as, e.g., described in U.S. Pat. No. 8,945,371), surface acoustic wave sensor, optical probe for measuring the evanescent wave, substrate surface coupled with an ultrasonic sensor for deposit thickness, tube sensor to measuring pressure drop, cartridge heated tube, or any combination of these devices. Deposit measurement may be conducted via the methods described herein as long as optical access is provided to a surface of a substrate, or the system can be modified to provide optical access. Implementing in-situ imaging to detect deposit formation provides a complementary measurement for proof-of-deposit, proof-of-surface cleanliness, information on the type of deposit based on color and morphology, qualitative assessment on the amount of deposit, and detecting the early onset of deposit formation. In certain embodiments, the substrate is capable of heating without the need for a separate heating element.

In certain embodiments, the substrate is a coupon. In certain embodiments, the substrate is a section of a conduit. In certain embodiments, the substrate is representative of a material of construction of the industrial water system. In certain embodiments, the substrate is constructed of a metal, which in certain embodiments is selected from steel, iron, aluminum, copper, brass, nickel, titanium, and related alloys. In certain embodiments, the steel is one of mild steel, stainless steel, and carbon steel. In certain embodiments, the metal is capable of passivation, and in other embodiments the metal is incapable of passivation.

The substrate contacts industrial water in an industrial water system, as shown in the figures, via flow channel 101. Examples of industrial water systems include, but are not limited to, heating water systems (e.g., boiler systems), cooling water systems (e.g., systems comprising a cooling tower), pipelines for water transport (e.g., seawater transport, which may be in transport to mining operations), and the like. Industrial water is any aqueous substance that is or will be used in an industrial water system. Generally, industrial water systems comprise industrial water that may be treated in some manner to make the water more suitable for use in the industrial water system of interest. For example, industrial water used in heating water systems (e.g., boiler systems) may be deaerated. The industrial water used in heating water systems may be further treated with, e.g., a deposit inhibitor, a corrosion inhibitor, a scale inhibitor, and/or a microbiological control agent. Other treatments may be rendered for various industrial water systems. In certain embodiments, the industrial water of the industrial water system is treated with a deposit inhibitor. In certain embodiments, the industrial water system is a cooling water system. In certain embodiments, the industrial water system is a heating water system, which may be a boiler system. In certain embodiments, the industrial water of the heating water system has been deaerated.

Examples of suitable deposit inhibitors include, but are not limited to, suitable antifoulants, antiscalants, and/or biocides.

The deposit inhibitor may be present in the industrial water at a concentration of from about 0.01 ppm to about 1000 ppm by weight, including from about 0.1 ppm or from about 1 ppm, to about 500 ppm, or to about 200 ppm.

Other substances may be present in the industrial water, including, but not limited to, one or more of a corrosion inhibitor, a buffer, other treatment chemicals and combinations thereof.

In certain embodiments, a parameter of the industrial water system is measured. Parameters include, but are not limited to, temperature, pressure, pH, conductivity, oxidation-reduction potential, linear polarization resistance, derivatives thereof, and combinations thereof.

The substrate is sufficiently lit to allow for creation of digital images of the substrate located in the industrial water system. In preferred embodiments, the substrate is sufficiently lit using one or more illumination sources, which may be a light-emitting diode, and, more preferably, a plurality of light-emitting diodes.

In the methods provided herein, a digital image, or series thereof, of the substrate is created. In certain preferred embodiments, the digital image, or series thereof, of the substrate is created while the substrate is located in an industrial water system. Though not preferred, the digital image, or series thereof, of the substrate can be created while the substrate is not located in an industrial water system. In the preferred embodiments, the substrate located in the industrial water system is generally in contact with the industrial water.

When utilized, the series of digital images may be two or more digital images. In certain embodiments, the series of digital images comprises a quantity of digital images sufficient to perform trend analysis of the digital images, and thus of the surface of the heated substrate. In preferred embodiments, series of digital images is a quantity sufficient to perform deposit trend analysis of the substrate. In certain embodiments, the series of digital images is created at a fixed time interval, i.e., each image is taken after a fixed amount of time has elapsed. In certain embodiments, the series of digital images is created at a fixed time interval when a parameter of the industrial water system is within a control limit, but the series of digital images is created at an interval of time less than the fixed time interval when the parameter of the industrial water system is not within the control limit. In other words, when the process is in control, a digital image is created at a rate of one digital image per t-length of time, but when the process is out of control, a digital image is created at a rate faster than one digital image per t-length of time.

In certain embodiments, the digital image, or series thereof, of the substrate is analyzed to determine a deposit trend of the substrate in the industrial water system. In certain embodiments, analyzing comprises defining a region of interest in the digital image, or series thereof, of the substrate and synthesizing trend data of the region of interest from the digital image, or series thereof. In some embodiments, analyzing comprises mathematical transformation of data to synthesize information related to size, color profile, percent area covered by deposit, overall mean surface area of deposit, heat transfer resistance (or increase thereof), related information (e.g., heat transfer coefficient, change in heat transfer coefficient, etc.), and combinations thereof, to calculate a deposit trend (e.g., a deposit rate). Deposit trending and examples of mathematical transformations of data are discussed further herein.

In certain embodiments, the methods comprise defining a region of interest in the digital image, or series thereof, of the substrate. The region of interest may comprise a surface of the substrate, or portion thereof. In certain embodiments, the region of interest is a surface, or portion thereof, of the substrate.

In certain embodiments, deposit develops on the region of interest, and thus, in certain embodiments, the region of interest comprises a deposit feature. In certain embodiments, the method comprises identifying a deposit feature in the region of interest. In certain embodiments, the surface area of the deposit feature is calculated, which can be analyzed to determine a deposit trend of the substrate in the industrial water system. The analysis may further include determination of the heat transfer resistance ("HTR"), which can be determined using the plurality of temperature probes. The analysis may further include measuring a parameter of the industrial water in the industrial water system selected from pH, conductivity, oxidation-reduction potential, linear polarization resistance, electrochemical corrosion monitoring, derivatives thereof, and combinations thereof. The analysis can be utilized to act to minimize or prevent deposit formation in the industrial water system.

In certain embodiments, action is taken based on the analysis of the deposit feature in the region of interest of the digital image, or series thereof, of the substrate, and optionally including, e.g., heat transfer resistance and/or any, one, combination of, or all of, the parameters listed herein. Generally, the action taken will be one or more action to prevent or lessen the effects of deposit in the industrial water system. Any one or more actions may be taken, including, but not limited to, increasing dosage of deposit inhibitor, selecting a different deposit inhibitor, modifying the deposit inhibitor, altering a physical property of the industrial water system, blowing down the industrial water system, shutting down the industrial water system, and combinations thereof.

In certain embodiments, a plurality of imaging devices is utilized to create a plurality of digital images, or series (plural) thereof. The plurality of systems could be configured to interface directly to, e.g., a controller that can be a PC, microprocessor, gateway, or combination of such devices to establish electronic communication for acquisition control as well as store and/or transmit image data. Data could be transmitted via wired connection and/or a wireless protocol (e.g., one or more of Wi-Fi, Zigbee, LoRa, Thread, BLE OnRamp, RPMA, the EEE 802.11 network family, IEEE 802.15.4, Bluetooth, HiperLAN, LoRa, etc.). Powering the systems can be via cable, battery, solar, or other energy harvesting means, e.g., vibration. The combination of using a wireless protocol with a self-powered method allows convenient installation at multiple locations. Image data collected by the controller can be stored, processed using advanced image analysis algorithms, processed and reduced to key trending variables, transmit data to a remote server, or communicate with a control device, e.g., a distributed control system ("DCS," e.g., Nalco 3D technology, available from Nalco Water, an Ecolab company, 1601 West Diehl Road, Naperville, Ill. 60563), a laboratory information management system (e.g., a "LIMS" software/hardware package), and/or a cloud computing system.

Creating the digital image can be acquired by simply taking a snap-shot of the substrate, and a series of digital images can be acquired by taking two or more snap-shots of the substrate over time. In certain embodiments, the digital images of the series of digital images are averaged, which can provide improved signal-to-noise ratio, which, for example, may be used to create a time-lapse video synchronized to process data collected by measuring a parameter of the industrial water in the industrial water system. The method may further comprise analyzing (e.g., synthesizing) the data collected from the digital image, or series thereof, by mathematically transforming the data, which in certain embodiments may provide further insight on the detected deposit.

The ability to capture the substrate image at different times provides a means to monitor the changes occurring on the substrate surface, in this instance, due to deposit. Furthermore, the ability to store image data provides the ability to compare current image data to past observations of different substrates of all kinds, e.g., similarly-situated substrates in the same industrial water system, similarly-situated substrates in different industrial water systems, statistical analyses of a population of substrates, and the like. For example, a series of digital images of a substrate can be created every 5, 10, 15 . . . days and analyzed against historical digital image data collected at the same incremental periods for one or more substrates located at the same position within the industrial water system. Observed differences between the data can indicate changes in the process due to the treatment program and/or water quality.

Utilizing digital image-processing algorithms can provide quantitative evaluation of the digital images, which provides quantitative evaluation of the deposit of the substrate, and therefore of the deposit of the industrial water system. Data collected from the digital image, or series thereof, can be used to develop overall trends related to a feature (or plurality thereof) on changes on the substrate surface area.

The methods and systems provided herein may be modified to allow for multispectral imaging, which in certain embodiments allows for characterization of the type of deposit formed on the substrate. In certain embodiments of the methods and systems provided herein, illumination of the substrate is made using narrow band wavelength light source such as a RGBW (red, green, blue, white) light emitting diode. Illumination of the substrate at different wavelength bands can highlight different colored regions that provide insight into classifying the type of deposit. Generally, the light source is limited to RGB, but a combination broad band light source with narrow band filters can be utilized to select certain more narrow wavelength bands. Alternatively, a multispectral imaging device, available from Surface Optics Corporation, 1155 Rancho Bernardo Rd., San Diego, Calif., may be utilized as the camera in the system, or to create the digital image, or series thereof, via multispectral imaging. Generally, a multispectral imaging device can provide continuous spectral information over a wavelength range from about 400 nm to about 1000 nm for each pixel. In embodiments that utilize multispectral imaging, the spectral range of the multispectral imaging device allows for identification of the type of deposit, e.g., mineral deposit (and possibly type of mineral deposit) versus microbiological deposit.

In certain embodiments of the methods and systems described herein, the substrate is a quartz crystal microbalance ("QCM") detector with the imaging system. For embodiments utilizing a QCM detector, the substrate described above and illustrated in FIGS. 1 and 2 is a QCM device operating at, e.g., 5 MHz. The QCM crystal counter electrode may be operated as a heating device to heat the electrode that is exposed to the fluid. Heating the electrode surface induces calcium carbonate deposit from an industrial water stream contacting the electrode surface, assuming that calcium and carbonate are present in the industrial water stream. As deposit forms on the surface, the resonant frequency of the QCM detector decreases due to mass loading following the Sauerbrey equation. Generally, heating of the QCM detector is stopped when the mass measurement is made. The QCM detector does not directly provide information on the composition of the deposit, but only the mass of the deposit.

Techniques using dissipation are commercially available, e.g., QCM-D from QSense part of Biolin Scientific USA, 215 College Road, Paramus, N.J., to determine whether the scale is soft (e.g., microbiological in nature) or hard (e.g., calcium carbonate). By coupling, an imaging system as shown in FIGS. 1-3 to a QCM detector in a configuration such as shown in FIGS. 1-3, insight into the type of scale formed on the surface may be obtained from the image data.

An example illustrating this point is shown in FIG. 4. The top series of images from left to right (increasing time) shows calcium carbonate deposit whereas the bottom series of images shows a brownish manganese and/or iron deposit on the surface determined from offline analysis. In both cases, the QCM sensor measured a mass increase over time. However, without feedback from the imaging system information about the nature of the deposit is lost. The additional insight on the deposit aids in treatment program chemistry and dosage optimization and validation of the effectiveness.

The water stress of the industrial water in the industrial water system may be tested, e.g., likelihood to form deposit as well as type of deposit, by operating the heated substrate at different surface temperatures as well as electrochemically changing the pH locally near the heated substrate surface. Furthermore, information related to water chemistry via alternate analysis, e.g., pH, conductivity, oxidation-reduction potential, treatment chemical consumption, alkalinity, metal ion concentration, phosphate, sulfate, and silica concentrations, may be input into a modeling software package, for example, French Creek Software, which, additionally may include input from the methods and systems described herein. For example, incrementally adjusting the temperature of the heated substrate to drive deposit formation on the heated substrate can provide information on the saturation level or deposit precipitation potential of the mineral salt in the industrial water. Additionally, a matrix of probe systems can be used in contact with, e.g., a single stream of industrial water with each probe set at a different operating condition, e.g., substrate temperature and/or local pH adjustment, as well as different substrate surface finish or metallurgy, etc.

In certain embodiments of the methods and systems described herein, the heated substrate comprises a glass-bonded mica block. In certain embodiments of the methods and systems described herein, the heated substrate comprises a polyetherimide resin (e.g., ULTEM resin, available from SABIC).

In certain embodiments of the methods and systems described herein, the heated substrate or a portion thereof is coated with temperature sensitive paint. When utilized, the temperature sensitive paint can provide additional accuracy in measurement of surface temperature of the heated substrate. Surface temperature of the heated substrate can be a critical parameter for measuring the water system scale potential because generally the operator attempts to reach conditions close to that found in a heat exchanger. Temperature sensitive paint is available as, for example, UniTemp temperature sensitive paint supplied by Innovative Scientific Solutions, Inc., 7610 McEwen Road, Dayton, Ohio. In certain embodiments, the surface of the heated substrate in contact with the industrial water is completely covered with temperature sensitive paint, and in other embodiments, one or more portions of the surface of the heated substrate in contact with the industrial water are covered. Generally, as the deposit forms on the surface and over the portion(s) of the surface covered with temperature sensitive paint, the emission intensity of the temperature sensitive paint will decrease due to reduction in the excitation source penetration to the temperature sensitive paint. Upon further deposit formation, the emission decreases, becoming less detectable since the deposit formed on the substrate will completely block the excitation source present in the temperature sensitive paint.

EXAMPLES

An application using the combination of heat transfer and imaging is demonstrated using a recirculated water system starting with the initial composition shown in Table 1, which is an experimental example of industrial water in an industrial water system. The water composition of Table 1 is utilized in all examples.

TABLE 1

Water composition for recirculating scale test system.

| Water Contents | ppm as CaCO3 | ppm as Substance | Water Recipe substance | mg/l (CaCO3) | Grams substance |
|---|---|---|---|---|---|
| Ca (CaCO3) | 550 | 220 | CaCl2—2H2O | 550 | 16.17 |
| Mg (CaCO3) | 225 | 54 | MgSO4—7H2O | 225 | 11.115 |
| Alkalinity (CaCO3) | 300 | 366 | NaHCO3 | 300 | 10.08 |
| Chloride (CaCO3) | 600 | 426 | NaCl | 50 | 1.17 |
| Sulfate (CaCO3) | 225 | 216 | | | |

Example 1

For this configuration water recirculated through a manifold with the system as shown in FIGS. 1-3 mounted in the flow loop that used flow rate control to maintain a flow rate at 1 gallon per minute for 1 inch Schedule 40 NPT pipe. To induce deposit formation, calcium carbonate concentration in the water was adjusted by adding 50 ppm calcium chloride and 100 ppm sodium bicarbonate at different increments. To benchmark the measurement a Bridger Scientific INC. DATS (Deposit Accumulation Test System) was installed on the recirculation loop. The probe used a Model HT19R 23 mm diameter 19 W ceramic heater from THORLABS, 56 Sparta Ave, Newton, N.J., to a 302 stainless steel substrate having a thickness of 0.01 inch. For temperature monitoring, type J thermocouples, model JMQSS-062G-6 from Omega Engineering INC., One Omega Drive, Stamford, Conn., were utilized. An additional RTD probe was used to measure bulk water temperature. Temperature logging was made on a United Electronics Industries, Inc., 27 Renmar Avenue, Walpole, Mass., DNA-PPC8 and DNA-AI-207 system connected to a personal computer. Flow rate monitoring and control was provided by the DATS unit, which was equipped with feedback flow control. Water conductivity, pH, and oxidation-reduction potential were continuously monitored using Nalco/ECOLAB 3D TRASAR control with probes inserted into a holding tank that fed and received the recirculated water.

Figure 5:
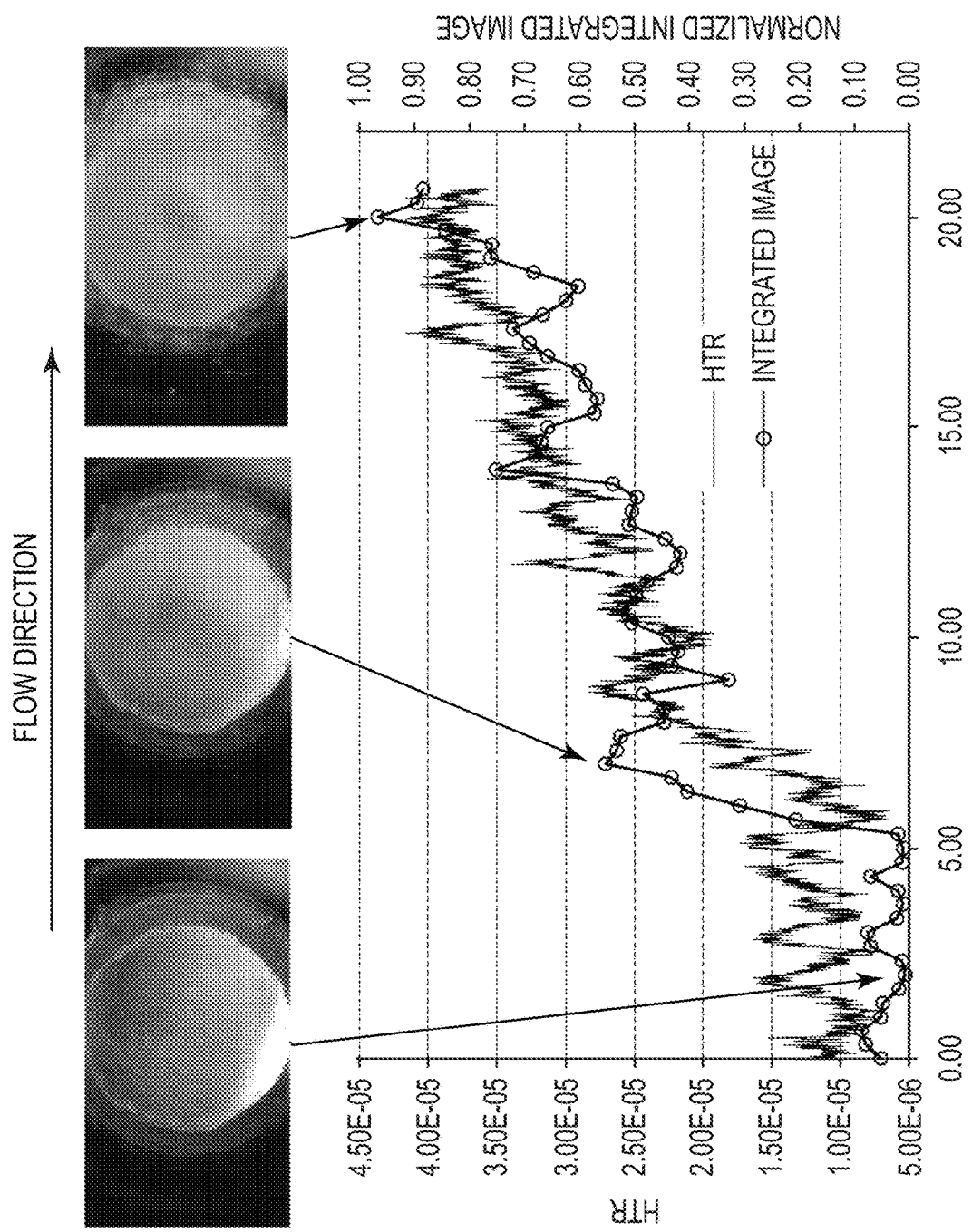
FIG. 5 shows examples of images corresponding to graphically tracked heat transfer reduction and reduced deposit image data of a substrate subject to a method described herein.
Figure 6:
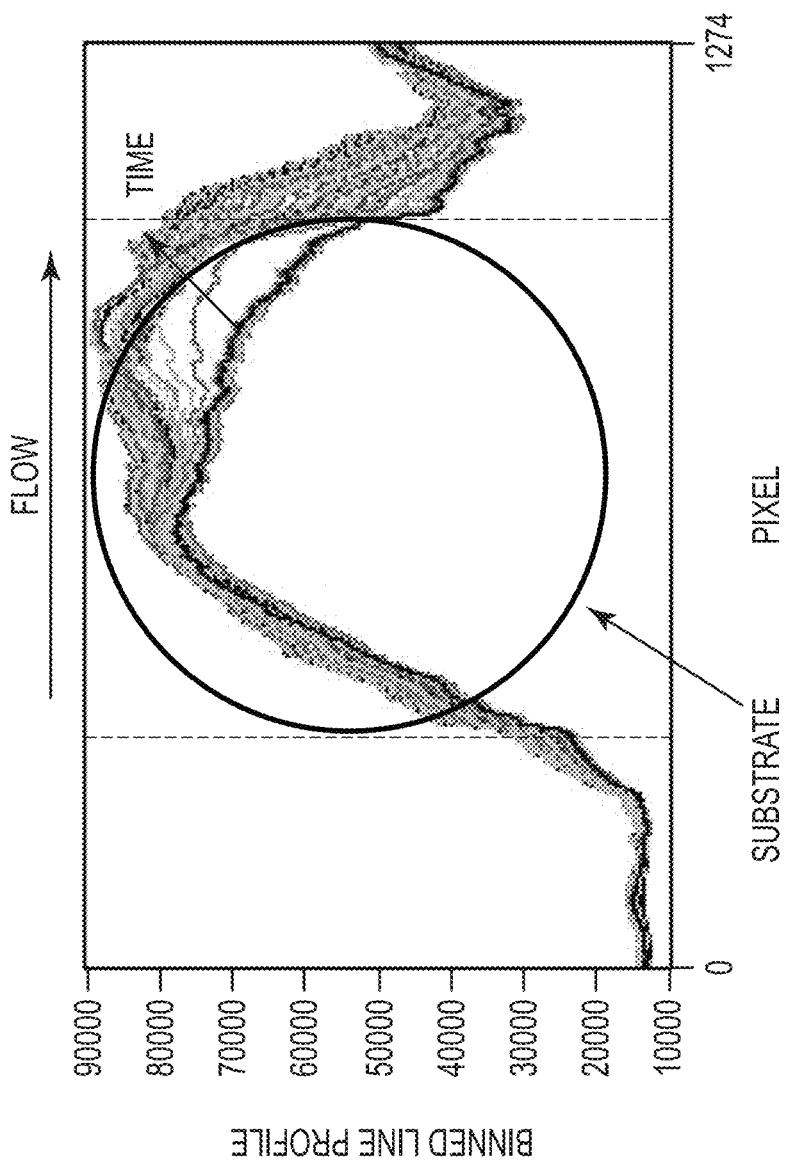
FIG. 6 shows an example of resulting binned image data collected over time of a substrate subject to a method described herein.
Figure 7:
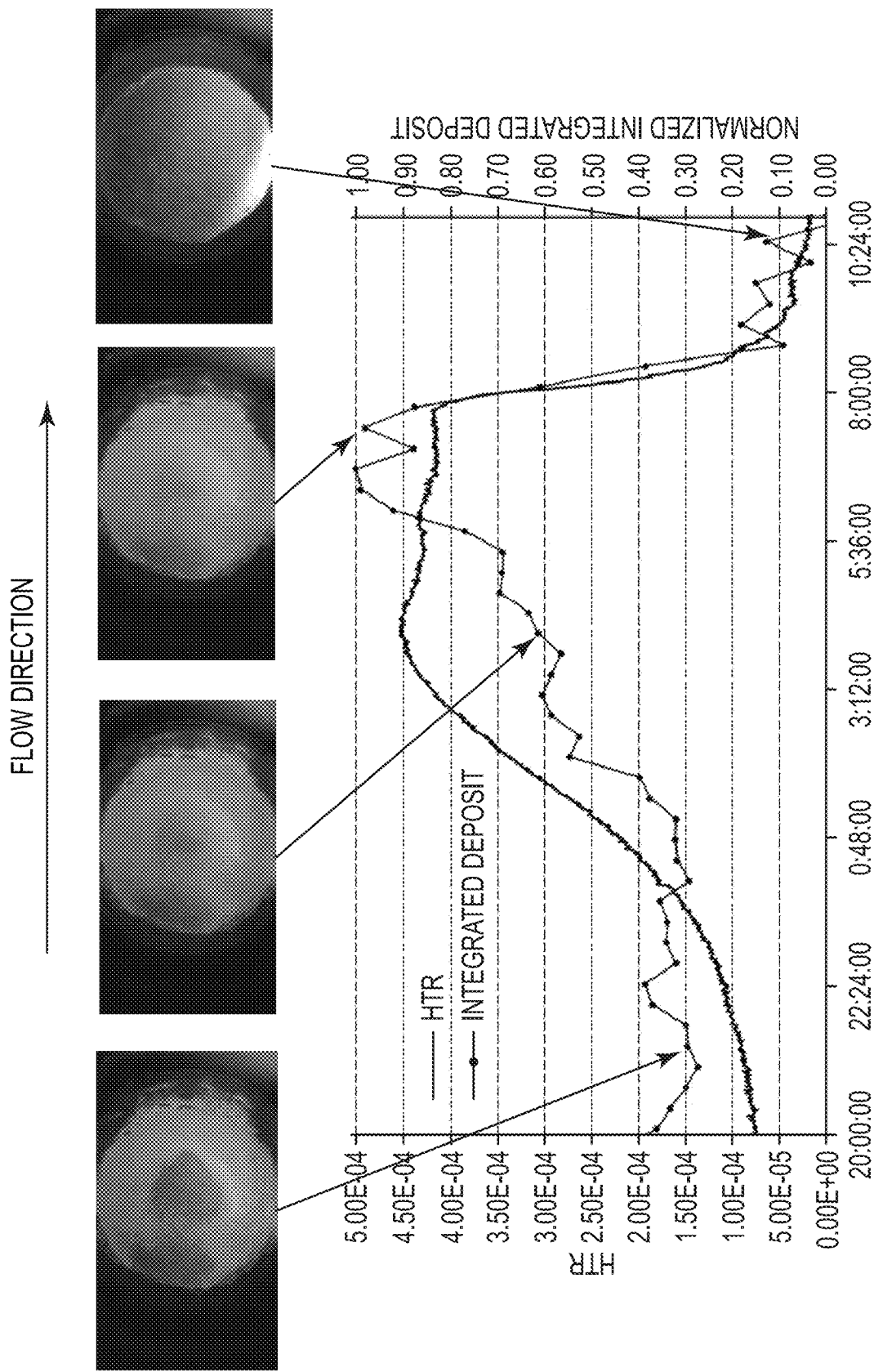
FIG. 7 shows examples of images corresponding to graphically tracked heat transfer reduction and reduced deposit image data of a substrate subject to a method described herein, wherein deposit removal is observed by decreasing pH of the industrial water.

Results from the experiment show the measured change in the heat transfer resistance, selected image data, and processed image data, which are presented in FIGS. 5-7. FIG. 5 shows the change in HTR is evident by the increasing value starting after 5 hours as deposit forms on the heated substrate. Simultaneously with the HTR measurement, the series of digital images shows the formation of deposit onto the surface of the heated substrate. Selected sample images are shown in FIG. 5 at different points in time. Image data is collected on a PC using a camera from THE IMAGING SOURCE LLC, 6926 Shannon Willow Rd, Charlotte, N.C., model DFK ECU010-M12 camera with a 8 mm lens from THE IMAGING SOURCE model TBL-8-C. Illumination was controlled with a Cree XLamp XP-E2 LED (Cree INC., 4600 Silicon Drive, Durham, N.C.) and Carlco 10140 lens (Carlco Optics, 600 Depot Street, Latrobe, Pa.). The example images show conditions before deposit is present (~2 hours), just after deposit began to form (~7 hours), and after an extend period (~20 hours) to show the extent of deposit formation on the surface of the heated substrate.

The series of digital images is processed to reduce the 2D image data (1280 Horizontal×720 vertical pixel resolution) to a single point that is plotted as a trend on FIG. 5 as the integrated image. Image processing steps involve first binning (i.e., summing) the pixel intensity values along the vertical direction to generate a horizontal intensity line profile from 0 to 1280 pixels. An example showing the resulting binned imaged data collected at different times is shown in FIG. 6. Also shown in FIG. 6 are vertical dashed lines that represent the edges of the substrate. The flow direction is from left to right indicated by the arrow on FIG. 6. The binned line profile is initially flat for all processed images because this is the unheated section to the left of the substrate, as observed in the image data shown in FIG. 5. The binned line profile between the dashed lines represents the substrate area and changes occurring on the substrate are observed in the intensity values of the line profile. As deposit forms on the substrate surface, the binned line profile increases over time. The largest change in the line profile is observed at the far right because this is the area where deposit formation occurs first, because this is the warmest region of substrate. Outside the substrate area to the right, the binned line profile shows more sensitivity than the left side due to deposit forming downstream in the direction of the water flow.

By integrating the line profile between the dashed lines shown in FIG. 6, the curve is reduced to a single point. When preformed at different time increments the integrated value can then be plotted as a trend. The value of the point is representative of the change in reflectivity and/or color of the substrate surface. FIG. 5 illustrates this point by comparing the integrated image data with the measured heat transfer resistances. As deposit forms on the substrate surface, HTR increases as well as the integrated image data with both showing a corresponding increase. The trend result shown in FIG. 5 is corrected for the offset, i.e., no deposit region, and normalized to the maximum integrated value to rescale the data from zero to one. In this example, the integrated image data detects the presence of deposit approximately 2 hours sooner than the HTR measurement based on using a detection limit of 2× noise level. In this case, the HTR noise is due to variations in the flow from the flow control system. Small variations in the flow rate propagate into the HTR calculation because of convection. Unlike HTR measurement, the image measurement is independent of fluid flow rate and/or temperature.

Example 2

In the second example shown in FIG. 7, a deposit is present on the substrate surface at the start of the plot. The deposit continues to form on the substrate surface resulting in HTR increasing, which plateaus at time of approximately 3:12, followed by a sharp decrease around 8:00 due to deposit being removed after introducing acid into the flow stream. The pH changed from 8.5 to less than 2. The integrated image data shows a similar trend but differs in the structure leading up to the acid injection. In both cases, after the deposit is removed from the substrate surface, the HTR and integrated image return to a baseline value that is less than the values at the beginning of the plot.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. In particular, the word "series" appears in this application and should be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of analyzing a deposit on a substrate contacting industrial water in an industrial water system, the method comprising:
    heating a substrate while the substrate contacts an industrial water in an industrial water system to a temperature higher than a temperature of the industrial water, thereby forming a deposit on the substrate;
    creating a series of digital images of the substrate while the substrate contacts the industrial water in the industrial water system;
    identifying a deposit feature in each of the series of digital images of the substrate; and
    analyzing the deposit feature in each of the series of digital images of the substrate to determine a deposit formation trend on the substrate in the industrial water system.

2. The method of claim 1, further comprising controlling treatment of the industrial water of the industrial water system with a deposit inhibitor based on the determined deposit formation trend.

3. The method of claim 1, further comprising determining a heat transfer resistance of the substrate.

4. The method of claim 1, further comprising measuring a parameter of the industrial water in the industrial water system selected from pH, conductivity, oxidation-reduction potential, linear polarization resistance, derivatives thereof, and combinations thereof.

5. The method of claim 1, further comprising measuring temperature at a plurality of points to determine heat transfer resistance of the substrate.

6. The method of claim 1, wherein the deposit comprises a calcium-containing substance.

7. The method of claim 6, wherein the calcium-containing substance is calcium carbonate.

8. The method of claim 1, wherein the deposit comprises an iron-containing substance.

9. The method of claim 8, wherein the iron-containing substance is ferric oxide.

10. The method of claim 1, wherein creating the series of digital images of the substrate comprises creating capturing multispectral digital images.

11. The method of claim 1, further comprising acting to control deposit formation in the industrial water system.

12. The method of claim 11, wherein the acting to control deposit formation in the industrial water system comprises taken an action selected from increasing dosage of a deposit inhibitor, selecting a different deposit inhibitor, modifying the deposit inhibitor, altering a physical property of the industrial water system, shutting down the industrial water system, and combinations thereof.

13. The method of claim 1, wherein analyzing the deposit feature comprises classifying the deposit feature on the substrate according to color.

14. The method of claim 1, further comprising moving the substrate in the industrial water system to expose a second region of interest to digital imaging; and repeating the steps of the method.

15. The method of claim 1, wherein the substrate is a quartz crystal microbalance.

16. The method of claim 1, wherein forming the deposit on the substrate comprises forming an inorganic deposit on the substrate.

17. The method of claim 1, wherein the industrial water system comprises at least one of a heat exchanger, a condenser, and a cooling tower, and heating the substrate to the temperature higher than the temperature of the industrial water comprises accelerating formation of the deposit beyond a rate at which the deposit would otherwise form on the at least one of the heat exchanger, the condenser, and the cooling tower.

18. The method of claim 1, wherein analyzing the deposit feature in each of the series of digital images further comprises determining a composition of the deposit based on at least one of a color of the deposit feature and a morphology of the deposit feature.

19. The method of claim 1, wherein the industrial water system is a heating water system or a cooling water system.

20. The method of claim 1, wherein the substrate is formed of metal.

* * * * *